US00PP36469P2

(12) United States Plant Patent
Boxriker

(10) Patent No.: US PP36,469 P2
(45) Date of Patent: Feb. 18, 2025

(54) ***OSTEOSPERMUM* PLANT NAMED 'KLEOE23403'**

(50) Latin Name: ***Osteospermum ecklonis* Norl.**
Varietal Denomination: KLEOE23403

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/779,349

(22) Filed: Jul. 22, 2024

(51) Int. Cl.
*A01H 5/02* (2018.01)
*A01H 6/14* (2018.01)

(52) U.S. Cl.
USPC ..... Plt./360

(58) Field of Classification Search
USPC ..... Plt./263.1, 360
See application file for complete search history.

(56) References Cited

U.S. PATENT DOCUMENTS

PP27,268 P2 * 10/2016 Klemm ..... A01H 6/14
Plt./360

* cited by examiner

*Primary Examiner* — Karen M Redden
(74) *Attorney, Agent, or Firm* — Weatherly IP Solutions, LLC; James M. Weatherly

(57) ABSTRACT

A new *Osteospermum* plant particularly distinguished by lavender flower color, with a white pattern under cold stimulation which otherwise is not visible or only slightly visible, with an upright habit and good branching, is disclosed.

1 Drawing Sheet

Genus and species: *Osteospermum ecklonis* Norl.
Variety denomination: 'KLEOE23403'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE23403'. 'KLEOE23403' originated from a cross-pollination conducted in summer 2015 in Nairobi, Kenya between the proprietary female *Osteospermum* variety 'KLEOE14226' (unpatented) and the proprietary male *Osteospermum* variety 'OE-2013-0357' (unpatented).

The seeds from the cross were collected and sown in Stuttgart, Germany in January 2016 and the plants were grown for evaluation. An individual plant designated 'KLEOE23403' was selected in April to May 2016 in Stuttgart, Germany. In June 2016 'KLEOE23403' was first vegetatively propagated by vegetative terminal cuttings in Stuttgart, Germany. 'KLEOE23403' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Lavender flowers, with a white pattern under cold stimulation which otherwise is not visible or only slightly visible;
2. Upright habit; and
3. Good branching.

DESCRIPTION OF THE PHOTOGRAPH

This new *Osteospermum* plant is illustrated by the accompanying photograph which shows a close-up of the foliage, buds, and mature flower. The photograph is of a 12-week-old plant grown outdoors in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLEOE23403'. The data which define these characteristics were collected in Stuttgart Germany in May 2024 on plants potted in October 2023. References are to The R.H.S. Colour Chart of The Royal Horticultural Society of London (R.H.S.), 5$^{th}$ edition (2007).

Classification:
- *Family*.—Asteraceae.
- *Botanical*.—*Osteospermum ecklonis* Norl.
- *Common*.—*Osteospermum*.
- *Designation*.—'KLEOE23403'.

Parentage:
- *Female parent*.—The proprietary female *Osteospermum* variety 'KLEOE14226' (unpatented).
- *Male parent*.—The proprietary male *Osteospermum* variety 'OE-2013-0357' (unpatented).

Plant:
- *Form and habit*.—Herbaceous perennial but usually cultivated as an annual; not frost resistant.
- *Growth habit*.—Upright.
- *Branching habit*.—Normal.
- *Height* (*from top of soil, including inflorescence*).—16.0 cm.
- *Width* (*including inflorescences*).—17.0 cm.
- *Propagation*.—Vegetative cuttings.
- *Time to produce a finished flowering plant*.—10 to 17 weeks.

*Time to initiate and develop roots.*—4 weeks.
*Root description.*—Fine; RHS 155A (white).

Leaves:
*Arrangement.*—Alternate.
*Shape.*—Obovate.
*Apex.*—Acute.
*Base.*—Acute.
*Margin.*—Entire.
*Immature color.*—Upper surface: RHS 137A. Lower surface: RHS 137C.
*Mature color.*—Upper surface: RHS 137B. Lower surface: RHS 137C.
*Length.*—3.5 cm.
*Width.*—1.9 cm.
*Texture.*—Upper surface: Leathery. Lower surface: Leathery with fine hairs.
*Petioles.*—Absent.
*Venation pattern.*—Absent.
*Venation color.*—Upper surface: RHS N144A. Lower surface: RHS 144A.

Stems:
*Total number of branches per plant* (*calculated at the base of the plant*).—7.
*Length.*—16.0 cm.
*Diameter.*—0.2 cm.
*Internode length.*—2.2 cm.
*Color.*—RHS 144A.
*Texture.*—Smooth.
*Anthocyanin.*—Absent.

Buds:
*Shape.*—Round.
*Length.*—1.2 cm.
*Diameter.*—0.8 cm.
*Color* (*at tight bud just before the ray florets unfold*) .—RHS 138A.

Inflorescence:
*Type.*—Composite, single.
*Blooming habit.*—Upright, with longer flower stems.
*Quantity of inflorescences per plant.*—4.
*Lastingness of the inflorescences on the plant.*—10 to 15 days.
*Fragrance.*—Absent.
*Inflorescence diameter.*—6.4 cm.
*Inflorescence depth.*—1.2 cm.
*Disc diameter.*—1.4 cm.

Disc floret:
*Quantity per inflorescence.*—Around 50.
*Shape.*—Tubular.
*Tube color.*—Closed: RHS N155A. Mature: RHS N155A.
*Length.*—0.7 cm.
*Diameter* (*at apex*).—0.1 cm.
*Apex.*—Acute.
*Apex color.*—RHS 90B.
*Base.*—Acute.
*Base color.*—RHS 145D.
*Margin.*—Entire.

Ray floret:
*Quantity per inflorescence.*—21.
*Shape.*—Oblanceolate.
*Color.*—Upper surface: RHS N80A with NN155C pattern, but only when there was a cold stimulation otherwise white pattern is not visible or only slightly. Lower surface: RHS N82B.
*Length.*—3.3 cm.
*Width.*—0.8 cm.
*Apex.*—Obtuse.
*Base.*—Acute.
*Margin.*—Entire.
*Texture.*—Upper surface: Smooth. Lower surface: Smooth.
*Peduncle.*—Length: 3.0 cm. Diameter: 0.2 cm. Texture: Smooth with hairs. Color: RHS 143C.

Phyllaries:
*Texture.*—Smooth with fine hairs.
*Color.*—RHS 137A.
*Arrangement.*—Single.
*Observed quantity per plant.*—18.
*Shape.*—Lanceolate.
*Color.*—Upper surface: RHS 137A. Lower surface: RHS 137B.
*Length.*—1.2 cm.
*Width.*—0.3 cm.
*Apex.*—Acute.
*Base.*—Obtuse.
*Margin.*—Entire.
*Texture.*—Upper surface: Smooth with fine hairs. Lower surface: Smooth.

Reproductive organs:
*Androecium.*—Location: On the disc floret. Stamens: Quantity: Numerous. Shape: Filamentous. Filament length: 0.4 cm. Filament diameter: Less than 0.1 cm. Anther: Shape: Lanceolate. Color: RHS 79A. Length: 0.4 cm. Diameter: Less than 0.1 cm. Pollen: Color: RHS 13A. Amount: Sparse.
*Gynoecium.*—Location: On the base of the petals (ray floret). Pistils: Number: Numerous. Length: 0.3 cm. Diameter: Less than 0.1 cm. Stigma: Color: RHS 79A. Shape: Filamentous. Length: 0.2 cm. Diameter: Less than 0.1 cm. Style: Color: RHS 79A. Length: 0.1 cm. Diameter: Less than 0.1 cm.

Fruit and seed set: None observed.

Disease and pest/insect resistance: No disease and pest/insect resistance observed.

COMPARISON WITH PARENTAL LINES AND KNOWN VARIETY

'KLEOE23403' is a distinct variety of *Osteospermum* and is distinguished from its parents as described in Table 1.

TABLE 1

Comparison with Parental Lines

| Characteristic | 'KLEOE23403' | Female Parent | Male Parent |
|---|---|---|---|
| Flower color | Lavender, with white pattern under cold stimulation which otherwise is not visible or only slightly | Pink | Purple |

'KLEOE23403' is most similar to the commercial *Osteospermum* variety 'KLEOE14235' (U.S. Plant Pat. No. 27,268). Differences between the varieties are described in Table 2.

TABLE 2

| Comparison with Similar Variety | | |
|---|---|---|
| Characteristic | 'KLEOE23403' | 'KLEOE14235' |
| Branching | Better than 'KLEOE14235' | Medium |
| Earliness | Early | Very early |

I claim:

1. A new and distinct variety of *Osteospermum* plant designated 'KLEOE23403' as illustrated and described herein.

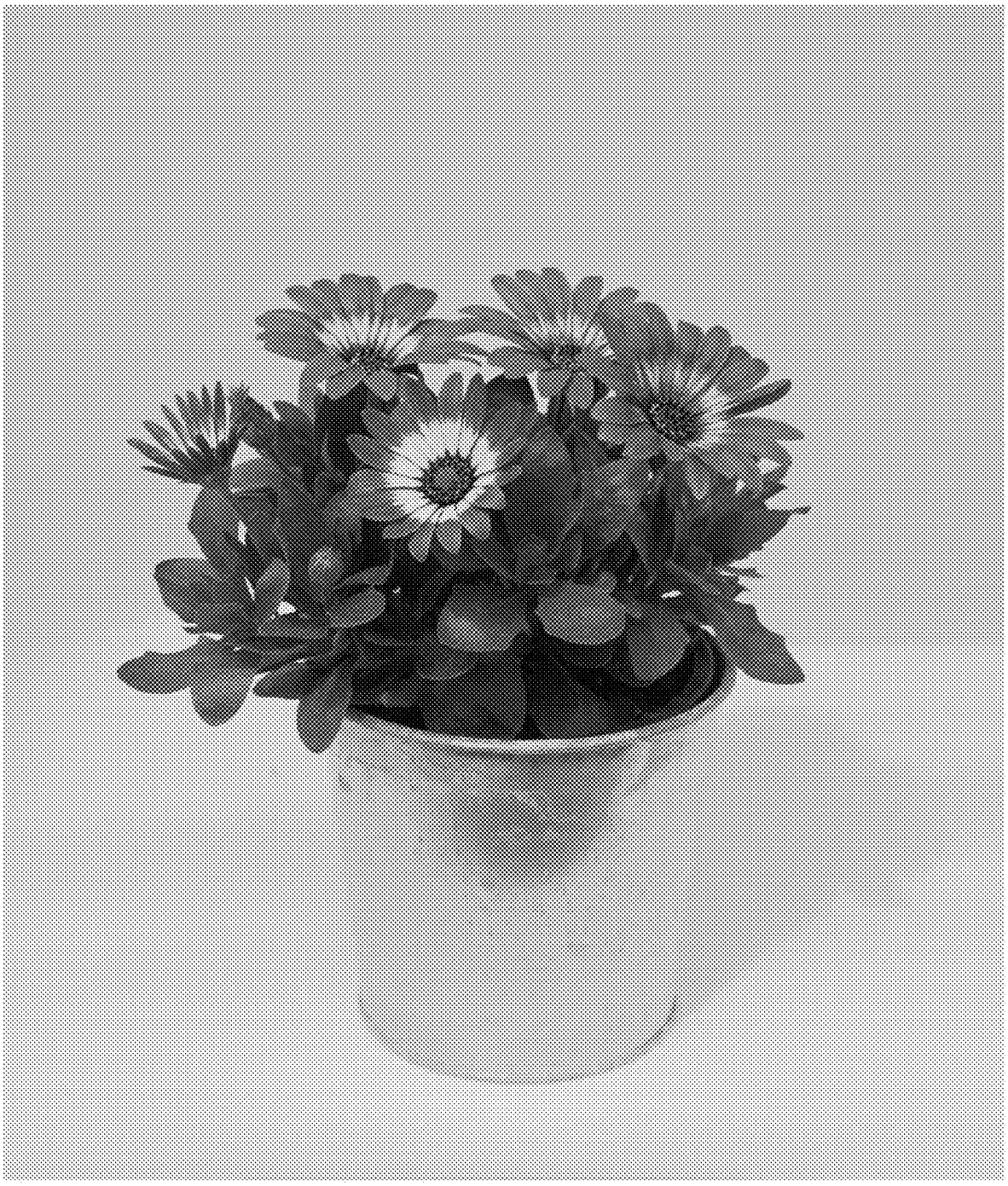

* * * * *